(12) United States Patent
Harttig et al.

(10) Patent No.: US 8,795,199 B2
(45) Date of Patent: Aug. 5, 2014

(54) PUNCTURING SYSTEM, LANCET RESERVOIR SYSTEM AND MANUFACTURING METHOD, AND METHOD FOR POSITIONING FUNCTIONAL ELEMENTS ON CARRIER TAPE

(75) Inventors: Herbert Harttig, Neustadt (DE); Bernd Hiller, Lampertheim (DE); Ahmet Konya, Waldsee (DE); Oliver Kube, Worms (DE); Hans-Juergen Kuhr, Mannheim (DE); Frederic Wehowski, Hockenheim (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 973 days.

(21) Appl. No.: 12/616,669

(22) Filed: Nov. 11, 2009

(65) Prior Publication Data

US 2010/0121369 A1  May 13, 2010

Related U.S. Application Data

(63) Continuation of application No. PCT/EP2008/003405, filed on Apr. 26, 2008.

(30) Foreign Application Priority Data

May 11, 2007 (EP) .................................. 07009456

(51) Int. Cl.
*A61B 5/151* (2006.01)
*A61B 5/157* (2006.01)
*A61B 5/15* (2006.01)
*G01N 35/00* (2006.01)

(52) U.S. Cl.
CPC ......... *A61B 5/15169* (2013.01); *A61B 5/15165* (2013.01); *A61B 5/15157* (2013.01); *A61B 5/15148* (2013.01); *A61B 5/15146* (2013.01); *A61B 5/1411* (2013.01); *G01N 35/00009* (2013.01)
USPC ........................... 600/583; 600/584; 606/181

(58) Field of Classification Search
CPC ............. A61B 5/1411; A61B 5/15146; A61B 5/15148; A61B 5/15157; A61B 5/15165; A61B 5/15169; G01N 35/00009
USPC .................................. 600/583, 584; 606/181
See application file for complete search history.

(56) References Cited

U.S. PATENT DOCUMENTS

| | | |
|---|---|---|
| 2005/0245845 A1 | 11/2005 | Roe et al. |
| 2006/0002816 A1 | 1/2006 | Zimmer et al. |
| 2006/0122536 A1 | 6/2006 | Haar et al. |
| 2007/0020143 A1 | 1/2007 | Seidenstricker et al. |
| 2007/0038150 A1* | 2/2007 | Calasso et al. ................ 600/583 |

FOREIGN PATENT DOCUMENTS

DE   102005022022 A1   12/2005
(Continued)

OTHER PUBLICATIONS

English Translation of corresponding PCT/EP2008/003405 International Preliminary Report on Patentability.

*Primary Examiner* — Rene Towa
*Assistant Examiner* — Emily Lloyd
(74) *Attorney, Agent, or Firm* — Bose McKinney & Evans LLP

(57) ABSTRACT

A puncturing system includes a carrier tape carrying multiple lancets and having position marks, a housing comprising a conveying facility for positioning the lancets and a housing opening, a puncturing drive for accelerating a lancet positioned in a usage position, a storage medium for storing distance values that depend on distances between the lancets of the carrier tape and position marks allocated to the respective lancets, a sensor for detecting position marks in a detection position through which the position marks proceed upon motion of the carrier tape, and a control unit that controls the conveying facility. To position a lancet in the usage position, the control unit stops the conveying facility upon the carrier tape moving a positioning distance. The length of the positioning distance depends on the distance between the lancet to be positioned and the detected position mark and is determined by the control unit.

21 Claims, 2 Drawing Sheets

(56) References Cited

FOREIGN PATENT DOCUMENTS

| | | |
|---|---|---|
| EP | 0371572 A2 | 6/1990 |
| EP | 1739432 A1 | 1/2007 |
| WO | 00/15653 A2 | 3/2000 |
| WO | 2004/047642 A1 | 6/2004 |
| WO | 2004/057345 A2 | 7/2004 |
| WO | 2004/060174 A2 | 7/2004 |
| WO | 2005/104948 A1 | 11/2005 |

* cited by examiner

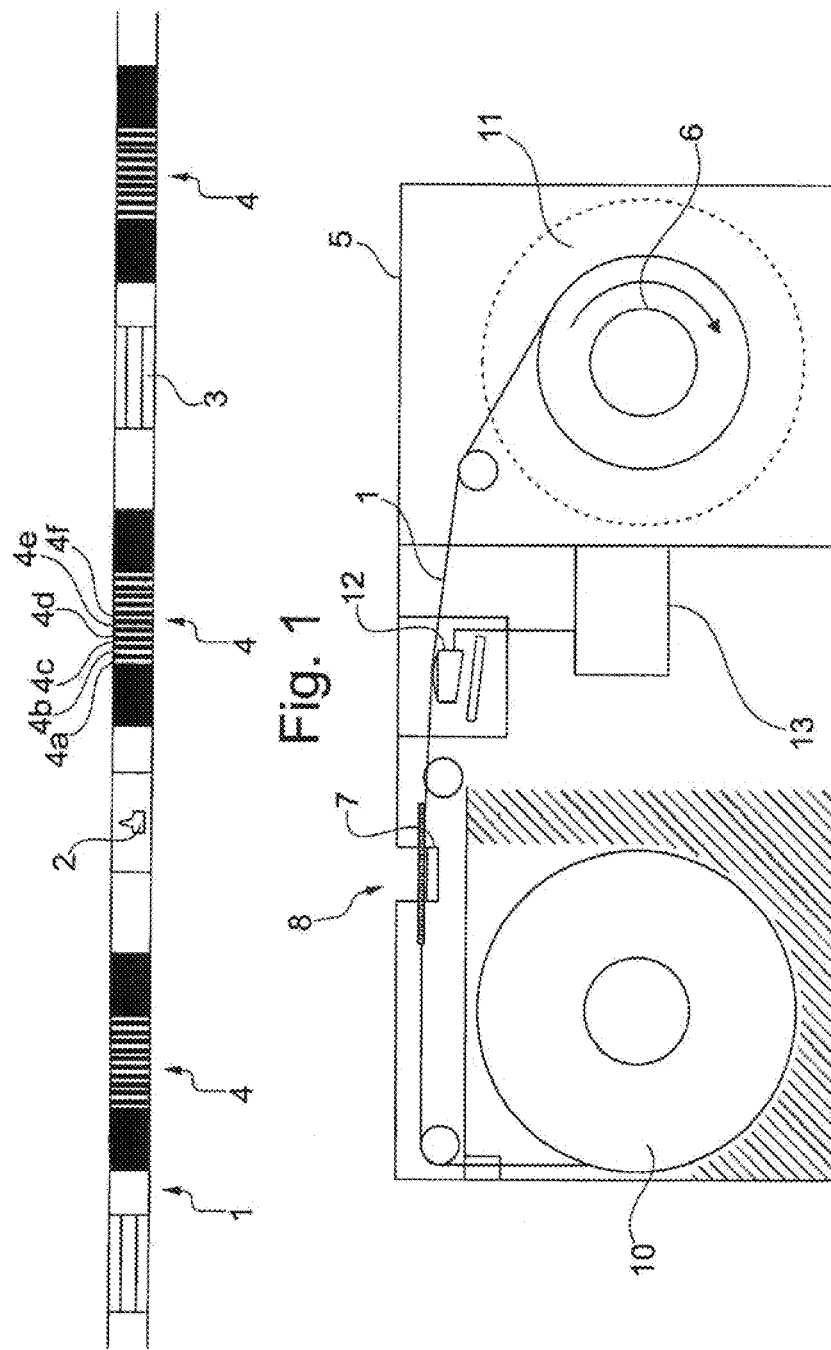

PUNCTURING SYSTEM, LANCET RESERVOIR SYSTEM AND MANUFACTURING METHOD, AND METHOD FOR POSITIONING FUNCTIONAL ELEMENTS ON CARRIER TAPE

CROSS-REFERENCES TO RELATED APPLICATION(S)

This application is a continuation of International Patent Application No. PCT/EP2008/003405, filed Apr. 26, 2008, which claims priority to European Application No. 07009456.0, filed May 11, 2007.

FIELD OF THE INVENTION

The present invention relates to the field of puncturing systems, lancet reservoirs and carrier tapes that carry multiple lancets.

DESCRIPTION OF RELATED ART

The present invention relates to puncturing systems. Puncturing systems can include, as a lancet reservoir, a carrier tape that carries multiple lancets. By moving the carrier tape in a conveying direction, the lancets are consecutively moved into a usage position, in which they can be accelerated by a puncturing drive for a puncturing motion such that a puncturing wound for obtaining a sample of body fluid can be generated in a body part that is touched against a housing opening of the puncturing system.

Puncturing systems of this type are used, for example, by diabetics who need to check their blood sugar level multiple times daily and, for this purpose, need a sample of body fluid, usually blood or interstitial fluid, that is obtained from a puncturing wound that is generated with a puncturing system.

Unlike puncturing systems having drum cartridges that typically contain only six or eight lancets, a carrier tape can form a lancet reservoir with a significantly larger number of lancets. Puncturing systems having a lancet reservoir in the form of a carrier tape are therefore advantageous in that a user more rarely needs to make the effort involved in exchanging a carrier tape or, if disposable devices are used, obtaining a new device.

To allow a lancet of a carrier tape to be punctured into a body part that is touched against a housing opening, the lancet must be positioned in a usage position with respect to the housing opening. The permissible positioning accuracies are relatively small in this context such that a significant effort is involved, especially if the carrier tape is very long.

It is therefore an object of the invention to devise a way that allows the lancets of a carrier tape in a puncturing system to be precisely positioned in a usage position with less effort.

This object is met by a puncturing system having the features specified in claim 1. The object is also met by a method for the manufacture of a lancet reservoir system having the features specified in claim 13, and by a method for the positioning of functional elements, in particular lancets, that are arranged on a carrier tape in a usage position, said method having the features specified in claim 14. Advantageous further developments of the invention are the subject matter of the dependent claims.

With regard to precise positioning in a usage position of test fields that are arranged on a carrier tape and can be used to test a sample of body fluid, it is known from EP 1 739 432 A1 to provide the carrier tape with position marks that allow the position to be detected during tape transport. Arranging the test fields precisely with respect to the position marks allows for precise positioning of the test fields in a usage position.

BRIEF SUMMARY OF THE INVENTION

It is against the above background that the present invention provides certain unobvious advantages and advancements over the prior art. In particular, the inventors have recognized a need for improvements in puncturing systems and lancet reservoirs comprising carrier tapes that carry multiple lancets.

Although the present invention is not limited to specific advantages or functionality, it is noted that according to the invention, lancets or other functional elements, for example test fields, that are arranged on a carrier tape are positioned in a usage position by means of position marks that are placed on the carrier tape. In the process, there is neither a need for the position marks to be arranged to be equidistant on the carrier tape at high precision, nor is there a need for the functional elements to always be arranged at precisely the same distance with respect to a position mark. Therefore, substantial cost savings can be reaped according to the invention in the manufacture of a carrier tape. Surprisingly, despite the imprecise arrangement on the carrier tape, it is feasible to position functional elements of a carrier tape in a usage position very precisely.

This is the case because, according to the invention, for each functional element a distance value is stored on a storage medium. The distance values each depend on the distance between the corresponding functional element of the carrier tape and a position mark allocated to it. According to the invention, a sensor is used to detect a position mark and then the distance value stored on the storage medium for the lancet to be positioned is used to determine how far the carrier tape with the functional element has to be moved now until the functional element reaches the usage position. It is preferable to always move the carrier tape in conveying direction only, i.e. forward. However, on principle, it is feasible just as well to move the carrier tape backward after detection of a position mark by a positioning distance whose length and direction are determined by the stored distance value.

The distance values each can specify the distance between a functional element and a position mark, in particular an adjacent position mark. However, it is feasible just as well that the position marks define set positions at which lancets or other functional elements are to be put down during fabrication, and that the distance values specify a deviation of the actual position of a functional element from the set position that occurred during fabrication. It can be provided, for example, to arrange functional elements at a set position exactly between adjacent position marks during fabrication of a carrier tape. Therefore, instead of specifying how far a functional element is situated from a closest position mark in or against the conveying direction, a distance value can, for example, just as well specify how far the respective functional element is situated from a set position in a given direction.

It is feasible just as well for the distance values to specify the length of a positioning distance, i.e. a distance by which the carrier tape still needs to be moved in order to position the functional element in the usage position when the corresponding position mark is detected by the sensor of the puncturing system. It is therefore not mandatory to actually calculate from a stored distance value the distance between the functional element and a position mark in order to position a functional element. It is sufficient to use the distance value to determine when the carrier tape needs to be stopped in order to precisely position a functional element in the usage position.

For determining the distance values for a carrier tape onto which lancets or other functional elements have been applied, it is preferred to measure the exact position of a functional element with respect to a position mark that has been allocated to it, preferably of the closest one against the conveying direction. The distance values can be placed, for example as bar code, on the carrier tape itself, for example on its backing. Storage medium that can abo be used include, for example, magnetic storage media, memory chips, RFID labels or other suitable data media. The storage medium can be placed either on the carrier tape itself or on a tape cartridge, which, according to its purpose, is inserted into a puncturing device. However, it is feasible just as well to provide the storage medium as a separate storage element.

According to the invention, not only lancets, but other functional elements that are positioned on a carrier tape, for example test fields for testing a sample of body fluid, can also be precisely positioned in a usage position. Therefore, one aspect of the invention relates to a method for the positioning of functional elements that are arranged on a carrier tape in a usage position by moving the carrier tape in longitudinal direction, characterized in that position marks placed on the carrier tape are detected by means of a sensor and, in response, a forward motion of the carrier tape by a positioning distance is effected, whereby the length of said positioning distance depends on the stored distance value that depends on the distance between the functional element to be positioned and the detected position mark.

A method of this type is used in a puncturing system according to the invention in order to position lancets in the usage position. Moreover, it can also be used in an analytical system that comprises a carrier tape with multiple test fields for taking up a sample of body fluid, and a device housing that contains a measuring facility for testing a sample of body fluid and a conveying facility in order to consecutively situate the test fields in a usage position by moving the carrier tape in a conveying direction, in which usage position the test fields can take up a sample of body fluid or act in conjunction with the measuring facility. An analytical system of this type is characterized by position marks that are provided on the carrier tape, a storage medium on which are stored distance values for the test fields that depend on the distance between a test field of the carrier tape and a position mark that is allocated to it, and a sensor for detecting position marks in a detection position through which the position marks proceed upon a motion of the carrier tape that is effected by the conveying facility, and a control unit that is connected to the sensor for controlling the conveying facility, whereby, in order to position a test field in the usage position, the control unit stops the conveying facility as soon as the carrier tape has been moved by a positioning distance in the conveying direction past a tape position, in which a position mark has reached the detection position, whereby the length of the positioning distance depends on the distance between the test field to be positioned and the detected position mark and is determined by the control unit by means of the distance value that is stored on the storage medium for the test field to be positioned. An analytical system of this type can be integrated into a puncturing system according to the invention or it can be realized independent thereof.

These and other features and advantages of the present invention will be more fully understood from the following detailed description of the invention taken together with the accompanying claims. It is noted that the scope of the claims is defined by the recitations therein and not by the specific discussion of features and advantages set forth in the present description.

BRIEF DESCRIPTION OF THE SEVERAL VIEWS OF THE DRAWING

The following detailed description of the exemplary embodiments of the present invention can be best understood when read in conjunction with the following drawings) where like structure is indicated with like reference numerals and in which:

FIG. 1 shows an exemplary embodiment of a carrier tape according to the invention;

FIG. 2 shows a schematic view of an exemplary embodiment of a puncturing system.

Figure 3:
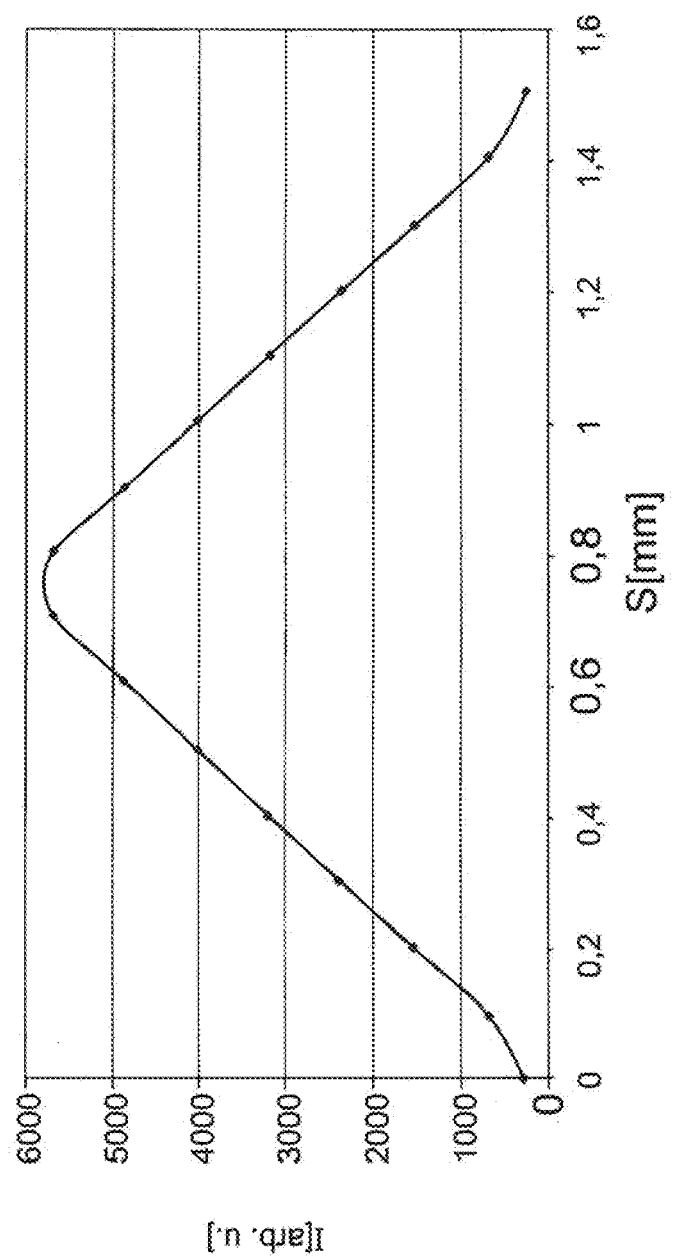
FIG. 3 shows an example of a sensor signal that results when a marking segment of a position mark of the carrier tape shown in FIG. 1 is guided past a sensor.

Skilled artisans will appreciate that elements in the figures are illustrated for simplicity and clarity and have not necessarily been drawn to scale. For example, the dimensions of some of the elements in the figures may be exaggerated relative to other elements to help improve understanding of the embodiments of the present invention.

DETAILED DESCRIPTION OF THE INVENTION

For the purposes of describing and defining the present invention it is noted that terms like "preferably", "commonly", and "typically" are not utilized herein to limit the scope of the claimed invention or to imply that certain features are critical, essential, or even important to the structure or function of the claimed invention. Rather, these terms are merely intended to highlight alternative or additional features that may or may not be utilized in a particular embodiment of the present invention.

The carrier tape 1 shown in FIG. 1 carries, as functional elements, lancets 2 and test fields 3, which each are arranged between lancets 2. The lancets 2 serve to generate a puncturing wound for obtaining a sample of body fluid that can be tested by means of a test field 3 for detecting or determining the concentration of an analyte. In the exemplary embodiment shown, the lancets 2 are oriented transverse with respect to the longitudinal direction of the tape 1. However, it is feasible just as well to arrange the lancets on the carrier tape such that their tips point in the longitudinal direction of the carrier tape 1.

A position mark 4 is placed on the carrier tape 1 for each functional element 2, 3. In the exemplary embodiment shown, the position marks 4 each are arranged between the functional elements 2,3. In principle, the number of position marks 4 can deviate from the circumstances shown. For example, it is feasible to provide only a single position mark 4 for two consecutive functional elements 2, 3 or to use more position marks 4 than in the exemplary embodiment presented.

In the exemplary embodiment shown, the position marks 4 each are made up by multiple marking segments 4a, 4b, 4c, 4d, 4e, 4f which are arranged adjacent to each other in the longitudinal direction of the tape. According to FIG. 1, the marking segments can be designed in the form of lines or just as well in a different geometrical shape, for example as dots. Variation of the position marks 4, for example of the thickness of the first marking segment 4a, can be used to identify whether the closest functional element in conveying direction is a lancet 2 or a test field 3.

During the manufacture of the carrier tape 1, the position marks 4 define set positions, in which the functional elements 2, 3 are to be arranged. In the exemplary embodiment shown, said set positions each are situated in the middle between position marks 4. During application of the functional elements 2, 3, it is tolerated, for the sake of rapid and cost-efficient fabrication, that at least some of the functional elements 2, 3 are placed on the carrier tape 1 with possibly substantial deviation from the set position defined by the position marks 4. Therefore, after the functional elements 2, 3 have been placed, the distance from a position mark 4 that is allocated to them is measured for the functional elements 2, 3, and a distance value determined therefrom is stored on a storage medium.

In the exemplary embodiment shown, the distance values depend on the distance between the tip of a lancet 2 and an adjacent position mark 4, preferably the next closest position mark 4 against the conveying direction. Distance values for test fields 3 depend on the distance between an edge of a field and an adjacent position mark 4, preferably the next closest position mark 4 against the conveying direction. The distance values are stored on a storage medium, for example as bar code on the backing of the carrier tape 1. It is feasible just as well to arrange a magnetic storage medium on the backing of the carrier tape 1 or to arrange the carrier tape in a tape cartridge that is designed to be inserted into a puncturing device, and to place the storage medium on the tape cartridge such that the distance values can be read by a reading device of a puncturing device into which the tape cartridge is inserted.

In this context, the conveying direction shall be understood to be the direction in longitudinal direction of the carrier tape 1, in which the carrier tape 1 needs to be moved in order to move unspent functional elements 2, 3 into the usage position and spent functional elements 2, 3 away from the usage position.

The carrier tape 1 and the storage medium on which the distance values are stored, taken together, form a lancet reservoir system. A lancet reservoir system of this type can be used with a puncturing device into which a carrier tape 1 of this type is inserted and which can be exchanged for a fresh carrier tape 1 once all lancets 2 are spent. However, the carrier tape 1 shown in FIG. 1 can just as well be used in a device that does not provide for the carrier tape 1 to be exchanged and is disposed as a so-called disposable device as soon as all lancets 2 of the carrier tape 1 have been spent.

FIG. 2 shows a schematic view of an exemplary embodiment of a puncturing system comprising the carrier tape 1 shown in FIG. 1. The carrier tape 1 is arranged in a device housing 5 that contains a conveying facility 6 for consecutively positioning the functional elements 2, 3 of the carrier tape 1 in a usage position by moving the carrier tape 1 in a conveying direction. Moreover, a puncturing drive 7 is arranged in the device housing in order to accelerate a lancet 2 that is positioned in the usage position for a puncturing motion which can be used to puncture into a body part that is touched against the housing opening 8. If a test field 3 is situated in the usage position in front of the housing opening 8, a sample of body fluid obtained by a puncture can be applied to it.

In the exemplary embodiment shown, the carrier tape 1 is reeled onto two rollers 10, 11 much like in an audio cassette tape. One of these two rollers is driven by the conveying facility 6 such that the tape is unreeled by the conveying facility 6 from the first roller 10 and reeled onto a driven second roller 11 and can, by this means, be moved in conveying direction. For example a stack, into which unspent sections of the carrier tape I are folded, can be used instead of the non-driven roller 10.

The carrier tape 1 proceeds past a sensor 12. The sensor 12 detects position marks 4 in a detection position through which the position marks 4 proceed during a motion of the carrier tape 1 that is effected by the conveying facility 6. In the exemplary embodiment shown, a position mark 4 is situated in the detection position, when it is situated directly in front of the sensor 12.

The sensor 12 preferably is an optical sensor since this allows the sensor 12 to also be used as measuring facility for photometric testing of a color change of a test field that is effected by an analyte that is contained in a sample of body fluid. Test fields for photometric detection or photometric determination of the concentration of analytes and matching measuring facilities are present in commercial devices for blood sugar monitoring such that more detailed explanations are not required. Using the measuring facility for photometric testing of a color change of a test field 3 and simultaneously as sensor 12 for detecting position marks 4 allows costs to be saved and the structure of the puncturing system to be simplified. However, it is feasible just as well to use position marks 4 that are not detected by optical means, for example magnetic position marks and corresponding magnetic sensors.

If an optical sensor 12 is used, it is particularly useful to detect position marks 4 in reflection. For this purpose, it is useful to make the position marks from a material with a reflectivity that is as high as possible, for example white paint or metal layers that produce a high contrast to areas of low reflectivity, in particular black areas. If an optical sensor measuring fluorescence is used, fluorescent pigments or fluorescence dyes can be used just as well. The position marks 4 can be printed onto the carrier tape 1. Basically all printing procedures are feasible. Screen printing, in particular cylinder screen printing, laser printing or ink jet printing are preferred. Metallic lines can be formed by transfer printing or, for example, by partial ablation of a metal layer that is previously vapor-deposited, for example by means of a laser.

The sensor 12 is connected to a control unit 13, which, for positioning a functional element 2, 3 in the usage position, stops the conveying facility 6 as soon as the carrier tape 1 has been moved by a distance in the conveying direction past a tape position, in which a position mark 4 has reached the detection position, whereby the length of said distance depends on the distance between the functional element 2, 3 to be positioned and the detected position mark 4 and is determined by the control unit 13 by means of the distance value stored on the storage medium for the functional element 2, 3 to be positioned. The control unit 13 can, for example, be an Application Specific Integrated Circuit (ASIC) or a microprocessor.

As mentioned above, the position marks 4 are made up of multiple marking segments 4a, 4b, 4c, 4d, 4e, 4f that are arranged adjacent to each other in longitudinal direction of the carrier tape 1. In FIG. 1, only the first 6 marking segments are labeled with reference numbers for exemplary purposes. The exact number of marking segments can be selected to a large extent freely. In the exemplary embodiment shown, multiple marking segments of the position marks 4 have identical extension in longitudinal direction of the tape. The position marks 4 shown in FIG. 1 have, as marking segments, consecutive light and dark areas which each have identical extension in longitudinal direction of the tape.

The sensor 12 comprises a light source, which, in operation, emits light that is focused onto a measuring spot on the carrier tape 1. In this context, the extension of the measuring spot in conveying direction of the carrier tape 1 deviates by not more than 30%, preferably by not more than 20%, from the extension in the conveying direction of one of said marking segments 4a, 4b, 4c, 4d, 4e, 4f. In the exemplary embodiment shown, the extension of the measuring spot in the conveying direction is identical to the corresponding extension of said marking segments. This measure is advantageous in that it allows a positional resolution to be attained that corresponds to just a fraction of the extension of a marking segment in the conveying direction. The resolution is essentially limited only by the precision and reproducibility of the width of the marking segments and the inaccuracy of the measuring spot diameter.

FIG. 3 shows an exemplary embodiment of a sensor signal that results when a marking segment is guided past the sensor 12. In this context, the signal intensity is plotted in arbitrary units (arb. u.) over the distances in millimeters traveled by the carrier tape 1. In this context, a maximal signal intensity is obtained exactly when a marking segment is covered completely by the measuring spot, since this results in maximal reflection. Only partial coverage of a marking segment by the measuring spot results in a correspondingly reduced signal. The signal is in this way analyzed in analog fashion. The peak of the sensor signal is used to deduce that a marking segment is covered completely by the measuring spot.

In order to position a functional element 2, 3 in the usage position, the tape 1 is first conveyed to a tape position, in which the position mark 4a is in the detection position and the sensor 12 produces a corresponding detection signal. From said tape position, the tape 1 then needs to be moved in conveying direction by a positioning distance, whose length depends on the distance value that is stored for the functional element 2, 3 to be positioned. In this context, the detection position can be defined by the sensor 12 reaching a first peak. In the exemplary embodiment shown, this is the case when the measuring spot of the sensor 12 completely covers the first marking segment 4a. However, it is feasible just as well to define the detection position, which, in combination with the distance value, specifies the positioning distance that is still required, such that the detection position is reached, for example, only at the second or third peak of the sensor signal.

The use of position marks 4 that are each made up of multiple marking segments allows the sensor 12 to produce a sensor signal that changes while the carrier tape 1 is moved by the positioning distance past a tape position, in which a position mark 4 has reached the detection position. In the exemplary embodiment shown, the extension of the position marks 4 in conveying direction is selected to be so large that it is larger than the positioning distances by which the carrier tape 1 still needs to be moved when the detection position has been reached, in order to position a functional element 2, 3 in the usage position. By this means, analysis of the changing sensor signal can be used to determine when the carrier tape 1 has been moved by the positioning distance and when, as a consequence, the conveying facility 6 has to be stopped. In this context, a tape section that carries the functional elements 2, 3 and is free of position marks extends between the position marks 4.

In order to position a functional element 2, 3 in the usage position, the conveying speed is reduced in the exemplary embodiment shown as soon as a first marking segment 4a is detected by the sensor 12. By this means, it can be determined at reduced speed and at higher precision when the position mark 4 has reached the detection position, i.e. when a predetermined marking segment is registered completely by the sensor 12. The second marking segment 4b can be used for this purpose, on principle. However, it has become evident that higher accuracy can be achieved if the second marking segment is used initially to calibrate the sensor 12. In the exemplary embodiment shown, the detection position is reached by a position mark 4 exactly when its third• marking segment4cis detected by the sensor 12.

The functional elements 2, 3, in particular the lancets 2, arc arranged on the carrier tape t between the position marks 4 at a positioning inaccuracy. The position marks 4 deviate from a set position aimed for in the fabrication process by a distance that is smaller than the extension of a position mark 4, i.e. of the marking segments of a position mark 4 taken together. If a position mark 4 is in the detection position, the distance of the lancet 2 allocated to it from the usage position is less than the extension in conveying direction of the position mark 4 with segments 4e, 4f that are not yet detected by the sensor 12. By this means, the distance value can be used to determine precisely how many marking segments of the current position mark 4 need to be guided past the sensor 12 until the lancet 2 has reached the usage position. Since the signal analysis procedures illustrated by means of FIG. 3 allow a positioning accuracy to be attained that is better than the extension of the individual marking segments in conveying direction, the carrier tape can be stopped exactly when the lancet 2 is positioned optimally.

Aside from the distance values, information concerning flawed functional elements 2, 3 or functional elements that are positioned on the carrier tape 1 outside an acceptable tolerance range can also be stored on the storage medium. 'Functional elements 2, 3 of this type can simply be passed over during operation of the puncturing system.

LIST OF REFERENCE NUMBERS

1 Carrier tape
2 Lancet
3 Test field
4 Position mark
4a Marking segments
4b Marking segments
4c Marking segments
4d Marking segments
4e Marking segments
4f Marking segments
5 Device housing
6 Conveying facility
7 Puncturing drive
8 Housing opening
10 Reeling roller
11 Reeling roller
12 Sensor
13 Control unit Having described the invention in detail and by reference to specific embodiments thereof, it will be apparent that modifications and variations are possible without departing from the scope of the invention defined in the appended claims. More specifically, although some aspects of the present invention are identified herein as preferred or particularly advantageous, it is contemplated that the present invention is not necessarily limited to these preferred aspects of the invention.

The invention claimed is:
1. A puncturing system comprising:
a carrier tape that comprises multiple lancets and position marks, each lancet being allocated a respective one of the position marks;

a storage medium configured to store distance values corresponding to measured distances between specific lancets of the carrier tape and the respective position marks;

a device housing that comprises a tape drive for positioning the lancets consecutively in a usage position by moving the carrier tape in a conveying direction and has a housing opening for touching against a body part in which a puncture is to be made by a puncturing motion of the lancet in the usage position;

a sensor configured for detecting the position marks;

a control unit that is connected to the sensor, the control unit configured to:

(i) cause the tape drive to convey the carrier tape to a tape position in which the respective position mark for one of the lancets is detected by the sensor;

(ii) access from the storage medium the distance value for the one lancet; and (iii) cause the tape drive to move the carrier tape in the conveying direction by the distance value for the one lancet, thereby positioning the one lancet in the usage position; and a puncturing drive for accelerating the lancet that is positioned in the usage position for the puncturing motion.

2. The puncturing system of claim 1 wherein the tape drive is configured to move the carrier tape only in the conveying direction.

3. The puncturing system of claim 1 wherein the sensor is configured to produce a sensor signal in response to the carrier tape being moved.

4. The puncturing system of claim 1 wherein the position marks comprise multiple marking segments that are arranged adjacent to each other in a longitudinal direction of the carrier tape.

5. The puncturing system of claim 4 wherein the marking segments are arranged at a distance that corresponds to their width.

6. The puncturing system of claim 4 wherein the sensor comprises a light source which is configured for projecting a measuring spot onto the carrier tape, wherein an extension of the measuring spot in the conveying direction of the carrier tape deviates maximally by 30% from the extension in the conveying direction of a respective marking segment.

7. The puncturing system of claim 6 wherein the extension of the measuring spot in the conveying direction of the carrier tape deviates maximally by 20% from the extension in the conveying direction of the respective marking segment.

8. The puncturing system of claim 1 wherein the sensor comprises an optical sensor.

9. The puncturing system of claim 1 wherein the carrier tape further comprises test fields for testing a sample of body fluid that is obtained from a puncturing wound, the test fields being arranged between the lancets on the carrier tape.

10. The puncturing system of claim 1 wherein the carrier tape further comprises test fields for testing a sample of body fluid that is obtained from a puncture wound, the sensor further comprising a measuring facility for photometric testing of a color change of a test field that is effected by an analyte that is contained in a sample of body fluid.

11. The puncturing system of claim 1 wherein the storage medium is configured to store information concerning individual lancets that are positioned on the carrier tape outside an acceptable tolerance range or are flawed.

12. A lancet positioning system, comprising:

a carrier tape that has multiple lancets and position marks, each lancet being allocated a respective one of the position marks;

a storage medium configured to store distance values corresponding to measured distances between specific lancets and the respective position marks;

a tape drive configured to move the carrier tape in a conveying direction to consecutively position the lancets in a usage position;

a sensor configured for detecting the position marks; and a control unit that is connected to the sensor, the control unit configured to:

(i) cause the tape drive to convey the carrier tape to a tape position in which the respective position mark for one of the lancets is detected by the sensor;

(ii) access from the storage medium the distance value for the one lancet; and (iii) cause the tape drive to move the carrier tape in the conveying direction by the distance value for the one lancet, thereby positioning the one lancet in the usage position.

13. The lancet positioning system of claim 12, wherein the tape drive is configured to move the carrier tape only in the conveying direction.

14. The lancet positioning system of claim 12, wherein the sensor is configured to produce a sensor signal in response to the carrier tape being moved.

15. The lancet positioning system of claim 12, wherein the position marks comprise multiple marking segments that are arranged adjacent to each other in a longitudinal direction of the carrier tape.

16. The lancet positioning system of claim 15, wherein the marking segments are arranged at a distance that corresponds to their width.

17. The lancet positioning system of claim 15, wherein the sensor comprises a light source which is configured for projecting a measuring spot onto the carrier tape, wherein an extension of the measuring spot in the conveying direction of the carrier tape deviates maximally by 30% from the extension in the conveying direction of a respective marking segment.

18. The lancet positioning system of claim 17, wherein the extension of the measuring spot in the conveying direction of the carrier tape deviates maximally by 20% from the extension in the conveying direction of the respective marking segment.

19. The lancet positioning system of claim 12, wherein the sensor comprises an optical sensor.

20. The lancet positioning system of claim 12, wherein the carrier tape further comprises test fields for testing a sample of body fluid that is obtained from a puncturing wound, the test fields being arranged between the lancets on the carrier tape.

21. The puncturing system of claim 20, wherein the sensor comprises a measuring facility for photometric testing of a color change of a test field that is effected by an analyte that is contained in a sample of body fluid.

* * * * *